United States Patent [19]

Lee et al.

[11] Patent Number: 5,332,503

[45] Date of Patent: Jul. 26, 1994

[54] PROCESS FOR PURIFYING COLLAGENASE

[75] Inventors: Catherine Lee, Laguna Hills; Cynthia Hornacek, Trabuco Cyn.; Tan T. Dinh, Garden Grove, all of Calif.

[73] Assignee: Baxter International Inc., Deerfield, Ill.

[21] Appl. No.: 73,272

[22] Filed: Apr. 16, 1993

[51] Int. Cl.$^5$ .............................................. B01D 15/08
[52] U.S. Cl. ..................... 210/635; 210/656; 435/41; 435/70.3; 435/219; 435/220; 435/226; 435/252.7; 435/815; 435/842
[58] Field of Search ............... 210/635, 656; 435/41, 435/70.3, 183, 219, 220, 226, 252.7, 267, 815, 842; 530/413, 416, 417

[56] References Cited

U.S. PATENT DOCUMENTS

| | | | |
|---|---|---|---|
| 3,201,325 | 8/1965 | Barton | 435/220 |
| 3,705,083 | 12/1972 | Chiulli | 424/94.67 |
| 3,821,364 | 6/1974 | Chiulli | 435/220 |
| 4,645,668 | 2/1987 | Pinnell | 424/94.65 |
| 4,745,183 | 5/1988 | Engelhorn | 210/656 |
| 4,752,578 | 6/1988 | Moore | 435/226 |
| 4,781,904 | 11/1988 | Tagaya | 423/308 |
| 4,794,171 | 12/1988 | Tagaya | 530/417 |
| 4,798,886 | 1/1989 | Kato | 530/416 |
| 5,106,743 | 4/1992 | Franzblau | 435/240.2 |
| 5,177,017 | 1/1993 | Lin | 435/220 |
| 5,252,481 | 10/1993 | Holjevac | 435/220 |

FOREIGN PATENT DOCUMENTS

| | | | |
|---|---|---|---|
| 60-013913 | 12/1986 | Japan | 210/656 |
| 2209526 | 5/1989 | United Kingdom | 210/656 |
| 91/14447 | 10/1991 | World Int. Prop. O. | 210/656 |

OTHER PUBLICATIONS

Bond and Van Wart, "Purification and separation of individual collagenases of clostridium histolyticum using red dye ligand chromatography", Biochemistry 1984, 23, 3077-3085.

Abstract of France Patent No. 2366306 from Food, Disinfectants, Detergents, Week A26, p. 6, 1978.

Primary Examiner—Ernest G. Therkorn
Attorney, Agent, or Firm—Poms Smith Lande & Rose

[57] ABSTRACT

A process for purifying crude collagenase is disclosed. The collagenase purification process includes providing a stabilized crude collagenase solution containing collagenase, pigment, toxins, bacterial materials, and proteolytic enzyme impurities including clostripain, trypsin, and caseinase. The stabilized collagenase solution is applied to hydroxylapatite packing. pigment and caseinase are eluted with a first solution comprising about 0.05 M to about 0.3 M phosphate buffer, and then collagenase, trypsin, and clostripain are eluted with a second solution comprising about 0.35 M to about 0.5 M phosphate buffer to provide a first collected solution. The first collected solution is then applied to gel filtration packing and collagenase and clostripain are eluted with a neutral pH buffer solution, to provide a second collected solution. The second collected solution is then applied to Reactive Red 120-Agarose packing and collagenase is eluted with a neutral pH buffer solution to provide purified collagenase. The process provides extremely pure collagenase in high yield with reduced consumption of eluting solutions and avoids unpredictable gradient eluting techniques.

16 Claims, 7 Drawing Sheets

PROCESS FOR PURIFYING COLLAGENASE

BACKGROUND OF THE INVENTION

1. Field of the Invention

The present invention relates generally to purified enzymes and improved processes for producing purified enzymes. More particularly, the present invention is directed toward the proteolytic enzyme, collagenase, and collagenase purification processes which are faster, provide higher yields of the purified enzyme, and retain the original collagenase isomer distribution.

2. Description of Relevant Art

Proteolytic enzymes are widely utilized in a variety of laboratory and clinical applications. Typically these applications involve cell dissociation and related therapeutic procedures which are benefitted by the ability of proteolytic enzymes to hydrolytically break-up or loosen connective tissue networks. For example, bacterial collagenase derived from *Clostridium histolyticum* has been used to disperse cells in laboratory tissue culture applications. Additionally, collagenase has demonstrated utility in cell isolation procedures such as those associated with isolating pancreatic islets and a variety of dispersed tumor cells. Other uses for collagenase involve its topical use in clinical applications in which collagenase compositions are applied in the treatment of burns or ulcers and in wound healing. Collagenase is also utilized in the treatment of Peyronie's disease, as an adjunct to cryoprostatectomy for the removal of retained cryoslough, in intervertebral discolysis, and in ophthalmic surgery.

Recently, bacterial collagenase derived from *Clostridium histolyticum* has found utility in procedures involving the dissociation and isolation of microvessel cells embedded in fatty tissues. These procedures generally involve combining fatty tissues having embedded microvessels, such as liposuctioned fat, with collagenase under conditions which cause the collagenase to disrupt and digest the connective tissue. Generally, the disruption process does not harm the membranes of the microvessel cells in the liposuctioned tissue, and by carefully separating the cells from the digested tissue, viable microvessel cells are recovered.

These viable and intact microvessel cells have found particular utility as a coating on the interior of synthetic small diameter vascular grafts for implantation in humans and animals to replace blood vessels. Similarly, microvessel cells are useful as deposits on the surface of biomedical implant devices in general where the cells provide improved biocompatibility to the implant devices. Apparently the microvessel cells contribute to the prevention of protein deposits and related cellular deposits on the implants which are known to occur when foreign materials are placed in contact with blood and tissues. In the case of vascular grafts, these deposits can quickly cause the vessel to occlude, resulting in the functional failure of the graft.

One problem associated with the use of commercial sources of crude collagenase to digest connective tissue is that the degree to which collagenase digests or hydrolyzes tissues is unpredictable. Moreover, cells which are isolated during tissue digestion and cell isolation procedures utilizing crude collagenase can be inferior in quality and have a low degree of viability and efficacy. Even when viable cells are successfully isolated, the yield and degree of viability is unpredictable.

The unpredictable nature of these procedures is attributed to the lot variations inherent in commercial sources of crude collagenase. Collagenase derived from native bacteria differs widely in its collagen specific hydrolytic activity and the amount and character of impurities, including other proteases and toxins. Most commercial collagenase is derived from the bacteria *Clostridium histolyticum* and in its crude form differs widely in hydrolytic activity and purity. Uncontrolled amounts of impurities found in crude collagenase include contaminating bacterial material, pigment, proteases, and peptidases, including clostripain, trypsin, and caseinase.

Unfortunately, protease impurities are active with proteins generally and will react with collagenase, causing the crude collagenase to be subject to catalytic degradation. Moreover, toxin impurities associated with crude collagenase can be a serious problem for procedures involving both in vivo and in vitro applications. Additionally, there may be present variable amounts of bacterial DNA, which potentially may cause immunologic or tumorigenic problems when isolated cells or tissue digestion procedures involve in vivo applications. Finally, the protein impurities found in crude collagenase may act as sensitizing antigens which can cause anaphylactic shock if administered to patients.

Thus, in view of the varying and unpredictable nature of crude collagenase compositions which contain a host of proteolytically active and unreactive compounds as well as toxins, therapeutic tissue digestion procedures and cell dissociation techniques using crude collagenase can be unreliable. Accordingly, procedures for efficiently and effectively isolating and purifying collagenase have been developed to provide predictably active collagenase with little or controlled amounts of impurities. Most collagenase purification procedures involve chromatographic separation of the contaminating proteases and unreactive components of crude collagenase.

One collagenase purification procedure in particular has gained recognition for the highly pure collagenase it provides. This procedure is described in Bond et al. "Purification and Separation of Individual Collagenases of *Clostridium histolyticum* Using Red Dye Ligand Chromatography" *Biochemistry*, Vol 23, No 13, 3077–3091, 1984, and involves chromatographic separation over various types of absorbents and gels to remove pigment and contaminating proteases. Significant drawbacks associated with this process are its time consuming steps and gradient elution techniques. In particular, the gradient elution procedures require large amounts of solvent and are difficult to reproduce with each purification procedure. Additionally, these procedures are plagued with cracked chromatography column packings which require frequent time-consuming repacking procedures and the loss of valuable reagents. Finally, prior art procedures do not effectively remove bacterial contaminants and many associated sensitizing antigens and toxins which can cause anaphylactic shock if even traces of crude collagenase are administered in vivo.

Accordingly, it is an object of the present invention to provide procedures for purifying crude collagenase which provide reproducibly pure collagenase capable of digesting connective tissue in a reproducible and predictable manner.

It is another object of the present invention to provide collagenase purification procedures which utilize reduced amounts of eluting solvent and provide pure enzyme in a reduced amount of time.

It is another object of the present invention to provide collagenase purification procedures which prevent cracking of chromatography column packing materials and to reduce the need for frequent repacking.

It is also an object of the present invention to provide collagenase purification procedures which remove bacterial contaminants and toxins associated with the bacterial contaminants.

SUMMARY OF THE INVENTION

The present invention accomplishes the above objectives by providing chromatographic purification procedures characterized by improved efficiency which reproducibly produce pure collagenase in high yield with substantially reduced consumption of elution solvent. The resulting pure collagenase will reproducibly and reliably contribute to tissue digestion and the isolation of embedded cells in a variety of therapeutic and laboratory applications. Collagenase purified in accordance with the present invention is free of toxins and unknown unreactive proteinaceous components, making the purified collagenase safe for in vivo use. Because the processes of the present invention effectively remove non-collagen active proteases which can degrade collagenase, the resulting pure collagenase has significantly reduced catalytic degradation characteristics. As a result, the purified collagenase has improved long-term stability properties and retains a high level of enzyme activity even when stored in solution.

Unlike prior art procedures which depend upon costly, time-consuming and difficult solvent gradient elution techniques, the processes of the present invention involve chromatographing crude collagenase preparations in batch steps using single ionic strength eluting solutions. Additionally, the present invention utilizes chromatography eluting solutions which stabilize and enhance the physical integrity and functional life of the packing material. Accordingly, the practice of the present invention provides essentially pure collagenase in high yield in a significantly reduced amount of time and at reduced material cost in a more reproducible manner.

More particularly, an exemplary process of the present invention includes the steps of providing a stabilized crude collagenase solution containing collagenase, pigment, toxins, bacterial material, and proteolytic enzyme impurities including clostripain and trypsin, applying the stabilized crude collagenase solution to a column containing a hydroxylapatite packing, and eluting pigment from the column with a first solution which comprises about 0.05 M to about 0.3 M potassium phosphate and a nonionic surfactant. The elution is continued until a substantial portion of the pigment is eluted from the hydroxylapatite packing. Then, the collagenase and proteolytic enzyme impurities are eluted from the hydroxylapatite packing with a second solution comprising about 0.35 M to about 0.5M phosphate buffer and a nonionic surfactant, to provide a first collected solution comprising collagenase and proteolytic enzyme impurities.

Next, the first collected solution is applied to a column containing a gel filtration packing and the column is eluted with a third solution comprising N-[tris(hydroxymethyl)-methyl]glycine (Tricine), $CaCl_2$ and NaCl, buffered to pH 7.5, to provide a second collected solution comprising clostripain and collagenase.

The second collected solution is then applied to a column containing a Reactive Red 120-Agarose packing and the column is eluted with a fourth solution comprising Tricine, $CaCl_2$, and NaCl, buffered to pH 7.5 to provide a third collected solution essentially comprising purified collagenase.

In accordance with the present invention, each of the eluting steps is carried out utilizing column chromatography techniques and apparatus. Accordingly, the packing utilized in each eluting step is provided in a chromatographic column and the chromatographic techniques involved with each chromatographing step are carried out utilizing general methods known in the art for separating components of a mixture on chromatography columns. Typically, the techniques involve packing a chromatographic column with selected packing material, equilibrating the column with an eluting solution, applying a sample for chromatographing, eluting with a selected eluting solution, and collecting and analyzing the eluant.

The purity of the collagenase in the third collected solution is demonstrated by the results of assays for each of the contaminating components. Accordingly, collagenase purified according to the present invention is free of pigment components as demonstrated by the lack of absorbance at 410 nm, since pure protein or enzyme does not display any absorbance at this wavelength. Similarly, there is an absence of nucleic acid material, as evidenced by the reduced ratio of the absorbance at 260 nm to that at 280 nm, and enzyme activities associated with the contaminating protease enzymes are negligible.

Because the purified collagenase of the present invention is essentially free of pigments, DNA, and non-collagenase active proteases, it exhibits predictable collagen degradation properties. Additionally, because toxins are effectively eliminated from the purified collagenase of the present invention, it is particularly useful in enzyme compositions used to isolate cells for subsequent in vivo therapeutic applications.

Further objects, features, and advantages of the present invention will become apparent to those skilled in the art from a consideration of the detailed description of exemplary embodiments taken in combination with the following drawings.

DETAILED DESCRIPTION OF EXEMPLARY EMBODIMENTS

The present invention provides improved chromatographic enzyme purification procedures which produce pure collagenase in high yield with a substantial reduction in process time and materials and a high degree of reproducibility. Collagenase purified according to the processes of the present invention will reproducibly and reliably contribute to tissue digestion and the isolation of tissue embedded cells in a variety of therapeutic and laboratory applications. Advantageously, the processes of the present invention avoid the consumption of large volumes of eluting solutions and annoying reproducibility problems associated with prior art gradient elution techniques. Moreover, the processes of the present invention avoid the risk of repacking chromatography columns and loss of samples during purification procedures by essentially eliminating annoying packing material cracking.

Moreover, the processes of the present invention provide methods for digesting and removing deoxyribonucleic acids and toxins associated with bacterial contaminants found in crude collagenase. Because the collagenase purified in accordance with the present invention is free of these bacterial impurities, it is useful for in vivo applications where the threat of anaphylactic reactions or related immunological complications are of concern. In particular, the purified collagenase of the present invention is useful for isolating microvessel cells embedded in fatty tissue for coating surfaces of biomedical implants to improve their performance.

Finally, collagenase purified according to the processes of the present invention is essentially free of non-collagen specific proteolytic enzymes and thus has significantly reduced autocatalytic degradation characteristics. This means that the purified collagenase has improved long-term stability and retains a high level of enzyme activity even when stored in solution.

The present invention is based upon the discovery that by chromatographing crude collagenase preparations in batch steps using single ionic strength eluting solutions, traditional time consuming gradient solvent elution methods which require large volumes of solvent are avoided. Moreover, by incorporating certain stabilizing additives and surfactants into eluting solutions, the chromatographic packing is provided with improved physical integrity and a longer functional life. Accordingly, the practice of the present invention provides essentially pure collagenase in high yield while significantly reducing the amount of time and reducing material costs associated with the procedure.

Figure 1A:
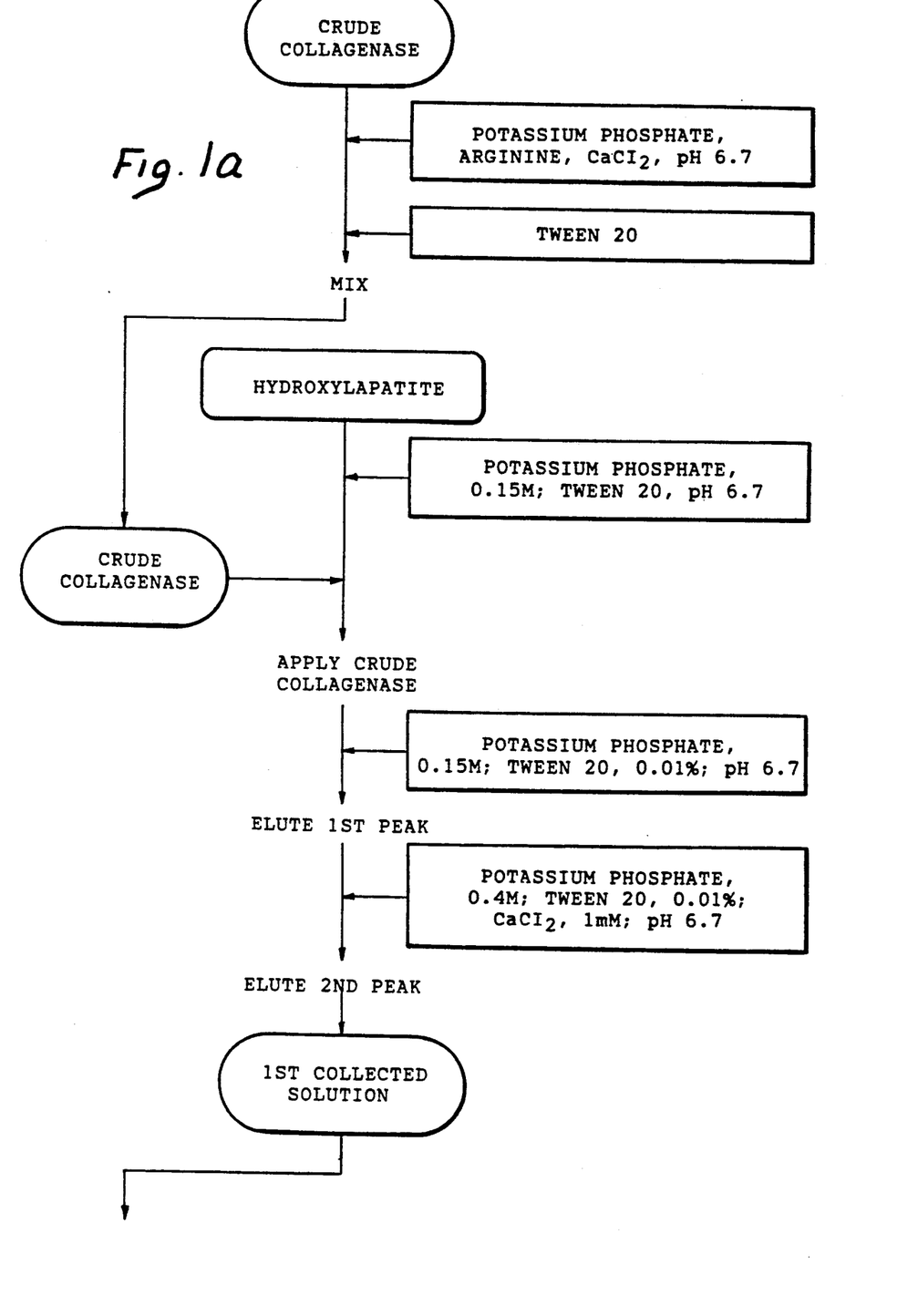
FIGS. 1A and 1B are flow charts illustrating an exemplary process in accordance with the present invention.
Figure 1B:
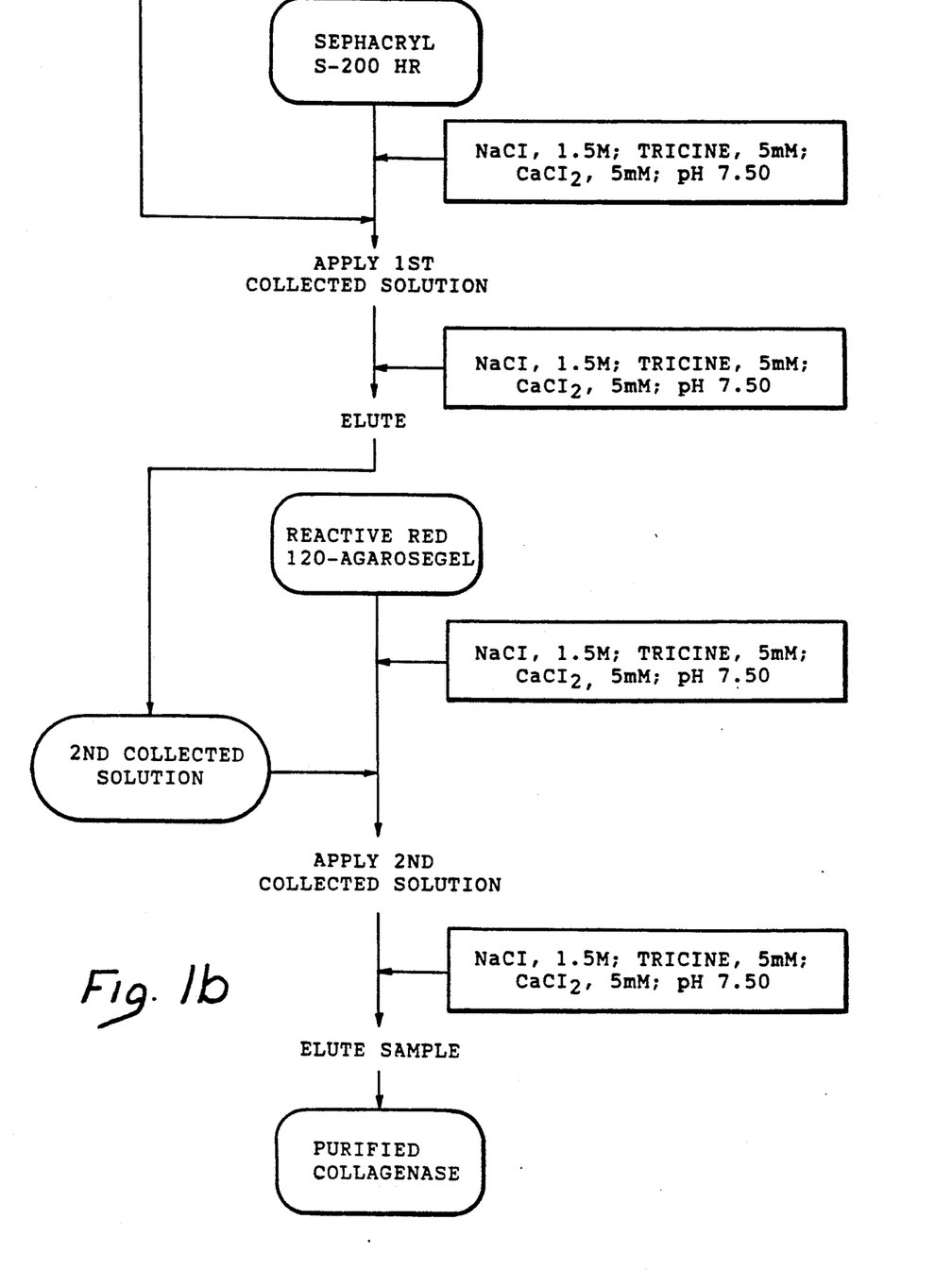
Figure 2A:
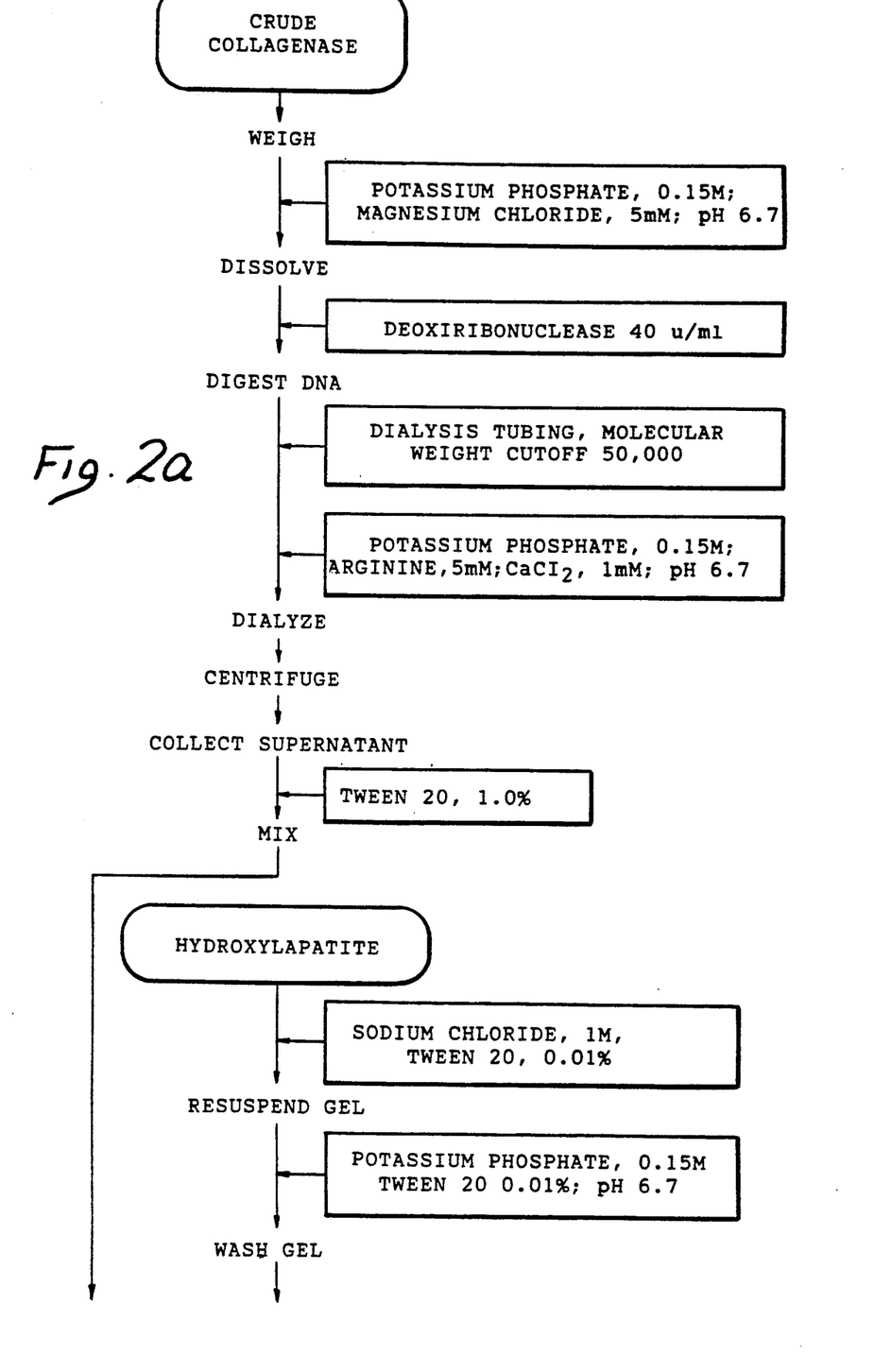
FIGS. 2A, 2B, 2C, 2D and 2E are flow charts illustrating an alternative exemplary process in accordance with the present invention.
Figure 2B:
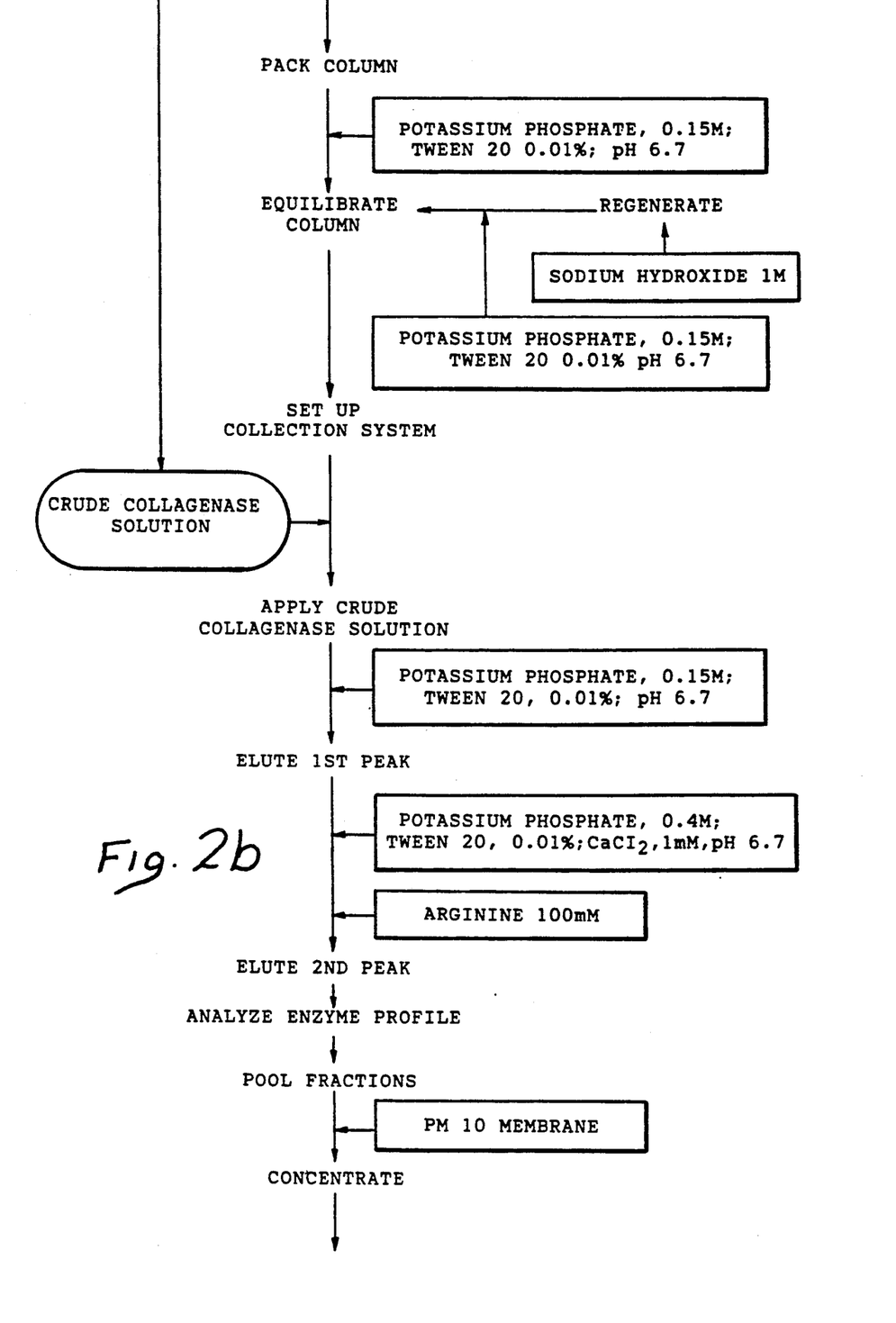
Figure 2C:
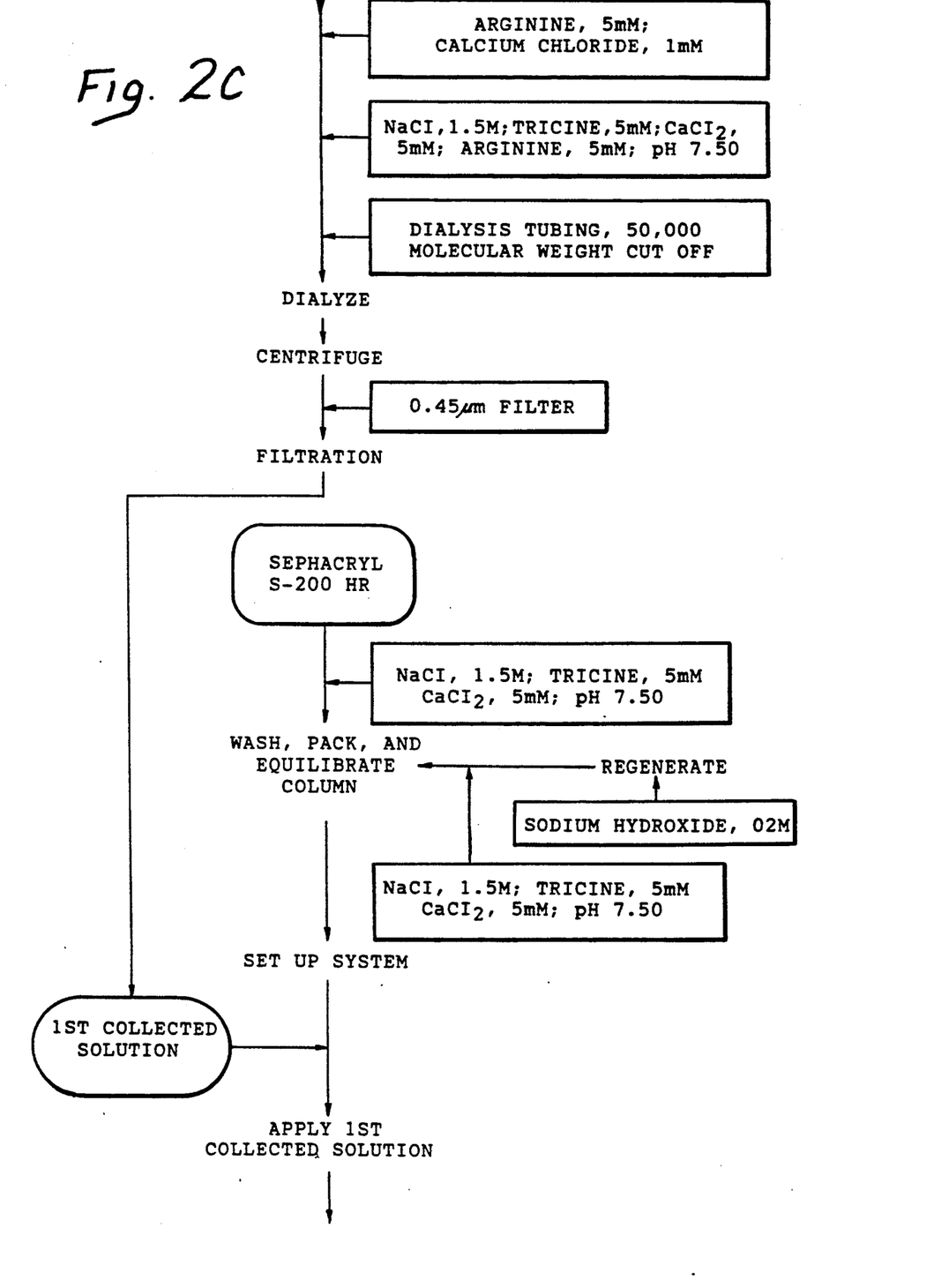
Figure 2D:
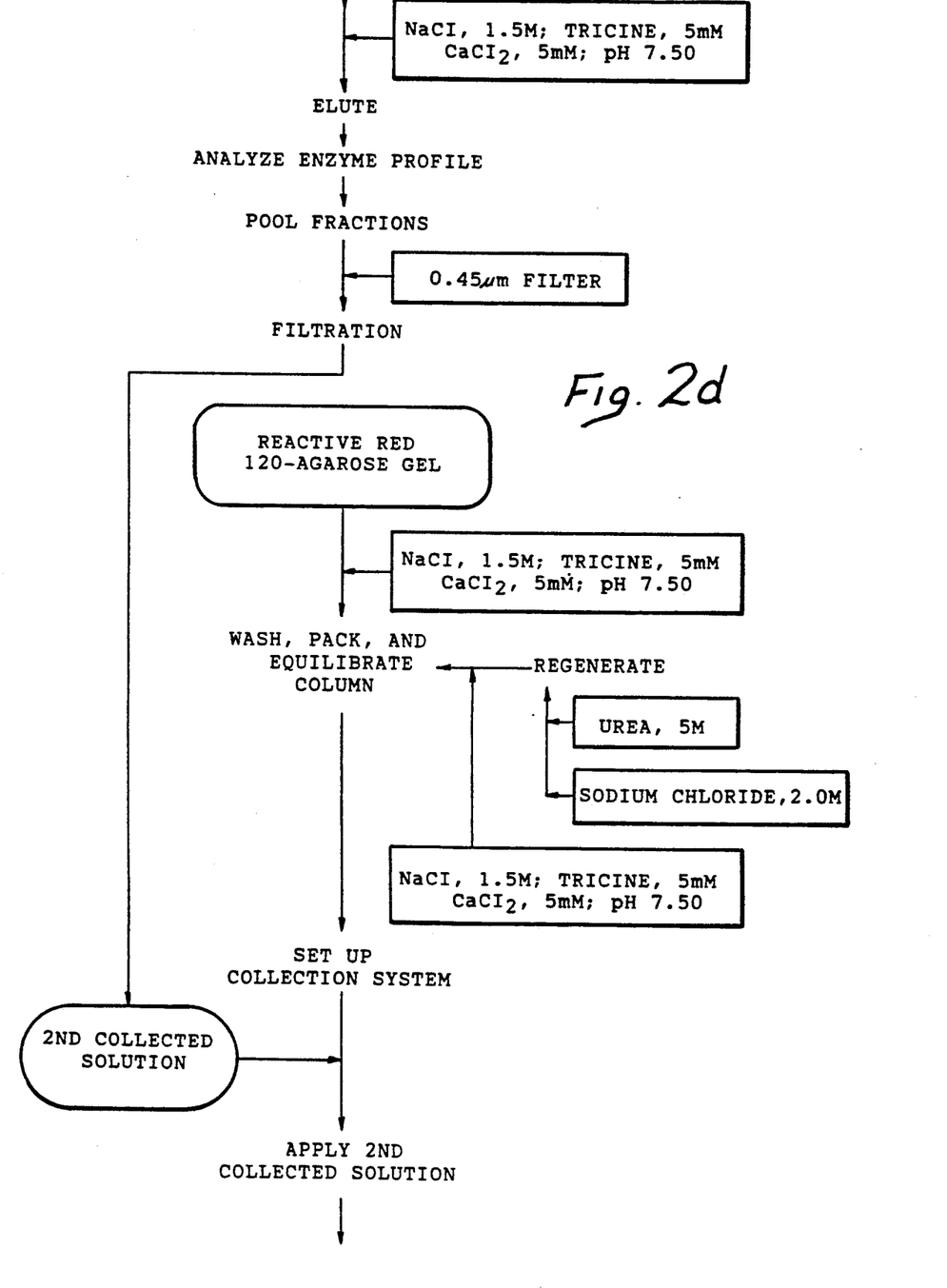
Figure 2E:
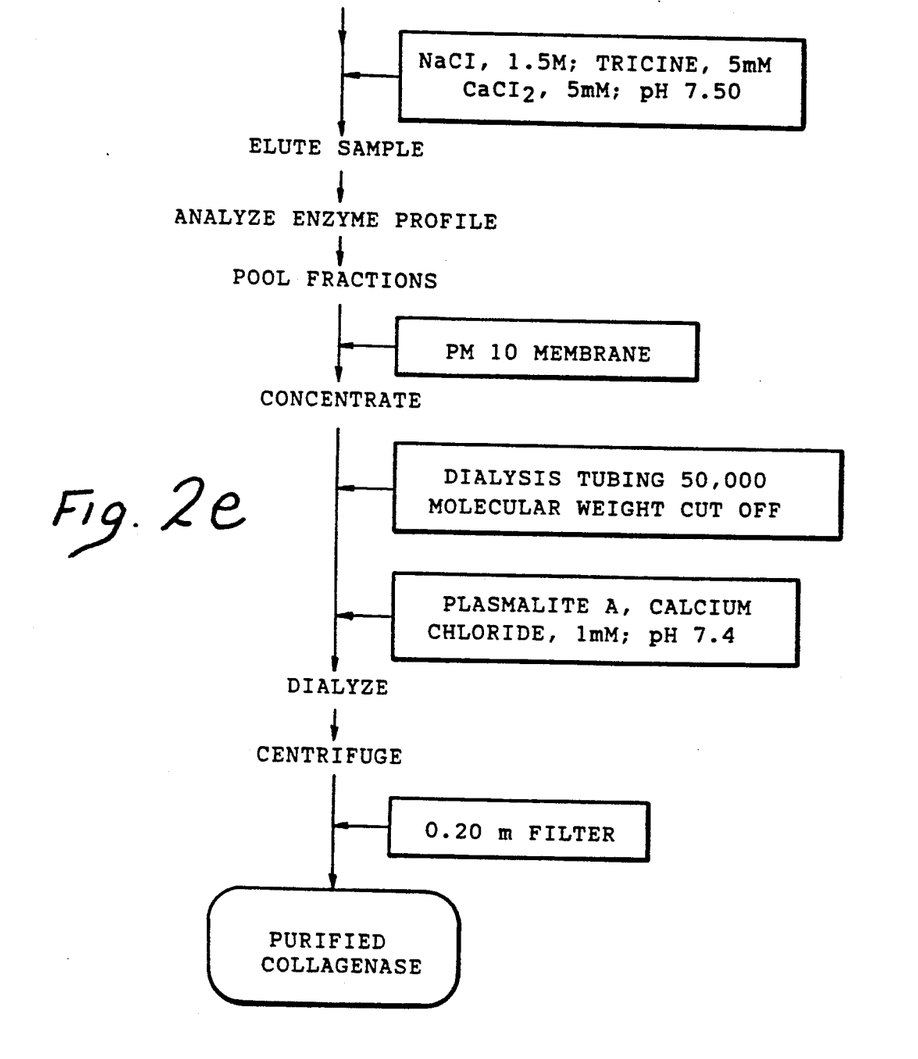

More particularly, the present invention provides enzyme purification processes useful for purifying collagenase compositions of collagenase, pigment, proteolytic enzyme impurities including clostripain and trypsin, and other bacterial materials. As illustrated in the flow diagram of FIG. 1, the exemplary processes of the present invention broadly include the steps of providing a stabilized crude collagenase solution that may include collagenase, pigment, bacterial toxic materials, and proteolytic enzyme impurities, and eluting the stabilized collagenase solution on a hydroxylapatite column with the first solution, which includes from about 0.05 M to about 0.3 M potassium phosphate and nonionic surfactant. The elution continues until a substantial portion of pigment is eluted from the hydroxylapatite column. Then, eluting the collagenase and proteolytic enzyme impurities on the hydroxylapatite packing with a second solution comprising at least 0.35 M phosphate buffer and nonionic surfactant provides a first collected solution of collagenase and proteolytic enzyme impurities. For purposes of the present disclosure, potassium phosphate refers to monobasic potassium phosphate and dibasic potassium phosphate present in amounts adjusted to provide the desired molarity (ionic strength) and solution pH in accordance with procedures known in the art. In preferred embodiments, the first and second eluting solutions have solution pH's of about 6.7. However, other pH's can be used as well.

The next step includes eluting the first collected solution on gel filtration packing with a third solution comprising N-[tris(hydroxymethyl)-methyl]glycine (Tricine), $CaCl_2$ and NaCl, adjusted to pH 7.5 with a suitable acidic or basic solution, to provide a second collected solution of clostripain and collagenase. Finally, eluting the second collected solution on Reactive Red 120-Agarose packing with a fourth solution comprising Tricine, $CaCl_2$, and NaCl, adjusted to a pH of about 7.5 provides a third collected solution of purified collagenase.

Those skilled in the art will appreciate that the above-described eluting steps of the present invention are preferably carried out utilizing liquid column chromatography procedures known in the art for separating mixture components on chromatography columns. Typically, these techniques involve packing a chromatography column with selected packing material, equilibrating the column with an eluting solution, applying a sample for chromatographing, eluting the sample with selected eluting solution, and collecting and analyzing eluant.

As described below, the combination of packing material and eluting solutions utilized in the present invention are central to providing purified collagenase. Preferred hydroxylapatite, gel filtration and Reactive Red 120-Agarose packings have the activity, purity and particle size suitable for column chromatography procedures. Accordingly, once suitably packed with the appropriate packing material, the packed columns can be equilibrated with a suitable eluting solution and then utilized to cause the separation of crude collagenase components in accordance with the present invention.

Hydroxylapatite packing material known to be useful in the practice of the present invention is available from a number of commercial sources including Bio-Rad. With respect to the gel filtration packing, any packing material which separates components of a solution by the size or molecular weight of the components is suitable. For purposes of the present invention, preferred gel filtration packings are the Sephacryl series and particularly, Sephacryl s-200 HR available from Pharmacia LKB Biotechnology. The preferred Reactive Red 120-Agarose gel is chromatography grade Reactive Red 120-Agarose gel, type 3000 CL, which is available commercially from Sigma Chemical Company.

As a feature of the present invention, the stabilized crude collagenase solutions include crude collagenase in an aqueous buffer containing $CaCl_2$ and arginine. The combination of $CaCl_2$ and arginine stabilizes the collagenase and suppresses the proteolytic activities of the trypsin impurities. This contributes to a reduction in the loss of collagenase activity due to proteolytic hydrolysis by trypsin which can hydrolyze collagenase rapidly in solution. Preferably, stabilized collagenase solutions include about 1 mM $CaCl_2$, about 5mM arginine and a suitable buffer, such as 0.15 M potassium phosphate buffer, pH 6.7. For purposes of the present disclosure, all references to potassium phosphate solutions having a specific pH generally refer to potassium phosphate salts including monobasic and dibasic potassium phosphate in combinations which provide the specific pH.

In accordance with the present invention, in order to enhance the ability of the hydroxylapatite column to remove bacterial DNA and toxins from the stabilized crude collagenase solution, DNase can be added to the stabilized crude collagenase solution prior to eluting it on hydroxylapatite. More particularly, by incorporating deoxyribonuclease into the stabilized crude collagenase solution in an amount sufficient to provide a deoxyribonuclease activity of about 40 u/mL, the large molecular weight nucleic acids present in the crude solution are digested. (One Kunitz unit will produce a $\Delta A_{260}$ of 0.001/min/ml at pH 4.6 at 25 C.) This step reduces the molecular weight of the nucleic acids and concurrently reduces the viscosity of the crude collagenase solution which aids in the chromatographic column fractionation.

As another feature of the present invention, it has been discovered that by incorporating a non-ionic surfactant in the stabilized crude collagenase solution and the first and second eluting solvents, the hydroxylapatite packing material has a reduced tendency to crack or change volume within the column. This is a common problem associated with hydroxylapatite columns when used with high concentrations of organic material. It is a particularly annoying problem because once the column cracks, it becomes useless and the whole procedure must be re-started. Moreover, this cracking problem can lead to the frequent loss of expensive materials and unrecovered reagents. The non-ionic surfactant apparently aids in maintaining a wetted packing material and maintains the eluting solvent uniformly passing over all the packing material. Any water soluble non-ionic surfactant which is compatible with collagenase is suitable for use in the present invention. The polysorbate non-ionic surfactants are particularly suitable, including the Tween 20 product, polyoxyethylenesorbitan monolaurate, available from Sigma Chemical Co.

Eluting the stabilized crude collagenase solution in accordance with the present invention involves applying the stabilized crude collagenase solution to the top of a hydroxylapatite packed liquid chromatography column, then causing the first solution to flow continuously through the hydroxylapatite. This eluting step is allowed to continue until the absorbance at 280 nm drops to below 10%. Those skilled in the art will recognize that the continuously flowing first solution is adjusted to flow at a rate which, by routine experimental evaluation, provides efficient separation of pigment from the remaining components of the stabilized crude collagenase solution. For purposes of the present invention, suitable eluting solution flow rates are from about 0.5 cm/hr to about 5 cm/hr.

Unlike prior art collagenase purification procedures which utilize gradient elution techniques to separate crude collagenase solutions on hydroxylapatite, the processes of the present invention include a two step elution technique on a packed hydroxylapatite column. More particularly, as described above, the stabilized crude collagenase solution is eluted on hydroxylapatite with a first solution having a potassium phosphate concentration of from about 0.05 M to about 0.3 M. Preferably, the first eluting solution is 0.15 M potassium phosphate having a pH of 6.7. Additionally, in order to continuously provide surfactant to the hydroxylapatite packing, preferred first eluting solutions further include 0.01 wt. % non-ionic surfactant. The solution ionic strength supplied by a 0.15 M potassium phosphate solution is sufficiently strong to elute the pigment impurities in the stabilized crude collagenase solution while retaining the other components found in the crude collagenase.

In the second step of the two step hydroxylapatite column eluting procedures, the second solution elutes the collagenase and any proteolytic enzyme impurities remaining on the hydroxylapatite after any pigment is eluted with the 0.15 M potassium phosphate solution. The second solution has a potassium phosphate concentration of at least 0.35 M and a preferred potassium phosphate concentration of 0.4 M with the potassium phosphate salts providing a pH of 6.7. For the same reasons stated above, the second solution preferably also includes 0.01 wt. % non-ionic surfactant. In contrast with the first solution which preferably has a much lower ionic strength of 0.15 M, the higher ionic strength associated with the second solution will rapidly sluts the collagenase and any proteolytic enzyme impurities including trypsin and clostripain from the hydroxylapatite to provide a first collected solution. Advantageously, by utilizing the two step eluting process as opposed to cumbersome gradient eluting process of the prior art, any pigment present is effectively separated from the crude collagenase solution utilizing much less time and much less eluting solution. This results in a less costly and more rapid procedure.

Those skilled in the art will also appreciate that the first collected solution of collagenase and proteolytic enzyme impurities are typically a pooled collection of fraction solutions. More particularly, eluting the collagenase and proteolytic enzyme impurities on the hydroxylapatite column typically involves collecting separate small volumes of eluant in the form of fractions and assaying each collected fraction for collagenase, trypsin, and clostripain activity according to assay procedures known in the art. Those fractions having enzyme activity are pooled to form the first collected solution for eluting on the gel filtration packing. This technique minimizes the possibility of unwanted impurities finding their way into the first collected solution and decreases the amount of eluting solvent in the first collected solution.

Eluting the first collected solution on a gel filtration column is accomplished by applying the first collected solution to a gel filtration column such as Sephacryl s-200 HR and eluting with the third solution which is preferably a solution comprising about 1.5 M NaCl, about 5 mM $CaCl_2$, and about 5 mM Tricine adjusted to a pH of 7.5. This eluting step causes trypsin to remain on the column longer, while enzymes having collagenase and clostripain activity are eluted to form a second collected solution. As with eluting the crude collagenase solution on hydroxylapatite, preferred procedures involve collecting fractions of gel filtration eluant, assaying the fractions for collagenase, trypsin and clostripain activities, and pooling fractions having significant collagenase activity and low clostripain activity, but no trypsin activity, to form the second collected solution.

The final eluting step in the purification procedure of the present invention involves eluting the second collected solution on Reactive Red 120-Agarose gel to separate the collagenase from any clostripain that may be present to provide purified collagenase. More particularly, this step is conducted by applying the second collected solution to a chromatographic column packed with Reactive Red 120-Agarose gel and eluting the column with a fourth solution which is preferably a solution comprising about 1.5 M NaCl, about 5 mM $CaCl_2$, and about 5 mM Tricine adjusted to a pH of 7.5. Advantageously, the ionic strength of the fourth eluting solution is such that collagenase does not bind to the Reactive Red 120-Agarose gel and it allows the collagenase to elute immediately without lengthy elution with salt gradients. Also, any clostripain or traces of pigment left in the second collection solution will strongly bind to the Reactive Red 120-Agarose gel as they require very high ionic strength solutions such as about 2 M NaCl and 5 M urea, for removal.

Those skilled in the art will further appreciate that procedures commonly associated with preparative liquid chromatography typically involve steps directed toward preparing the chromatography packing and to regenerating the chromatography packing subsequent to its use. Accordingly, preferred processes of the present invention further include methods for preparing the preferred hydroxylapatite columns, Sephacryl gel filtration columns, and Reactive Red 120-Agarose gel columns. For example, preparing the columns may be accomplished by suspending hydroxylapatite column packing material in a solution comprising 1 M NaCl and about 0.01 wt. % Tween 20 and then washing the suspended packing material in a solution comprising 0.15 M potassium phosphate and about 0.01 wt. % Tween 20 adjusted to a pH of 6.7 provides hydroxylapatite suitable for packing into a chromatographic column. Subsequent to packing the chromatographic column according to methods known in the art, the next step includes equilibrating the hydroxylapatite packed column by allowing a solution comprising 0.15 M potassium phosphate and about 0.01 wt. % Tween 20 adjusted to a pH of 6.7 to flow through the packing material.

Similar suspending and equilibrating methods may be utilized to prepare the gel filtration and Reactive Red 120-Agarose packing material. For example, suspending Sephacryl s-200 HR or Reactive Red 120-Agarose packing material in a solution comprising 1.5 M NaCl, 5 mM Tricine, 5 mM $CaCl_2$ buffered to a pH of 7.5 and then packing and equilibrating the column with an equilibrating aqueous solution similar to the aqueous suspending solution provides a suitably prepared Sephacryl s-200 HR packed column for eluting the first collected solution. As illustrated in the detailed flow diagram of FIG. 2, the suspending and equilibrating solutions described above apply to preparing the Reactive Red 120-Agarose packing material for eluting the second collected solution as well.

Methods directed toward regenerating column packing material are typically carried out at a time when the packing material has been in use sufficiently long to decrease its effectiveness for separating components of solutions eluting on the column. For purposes of the present invention, for example, spent hydroxylapatite packing material is regenerated after each purification step. Preferred hydroxylapatite regeneration methods involve causing a solution comprising 1 M sodium hydroxide to flow through the hydroxylapatite and then causing a solution comprising 0.15 M potassium phosphate and about 0.01 wt. % Tween 20 adjusted to pH 6.7 to flow through the spent hydroxylapatite. Following these two steps, the packing material is ready for equilibrating according to the procedure described above.

Regenerating gel filtration packing material utilized in the present invention is accomplished using aqueous regenerating solutions similar to those utilized for regenerating the hydroxylapatite packing material. More particularly, by sequentially causing a solution comprising 0.2 M sodium hydroxide to flow over spent Sephacryl s-200 HR packing, and then a solution comprising 1.5 M NaCl, 5 mM Tricine, and 5 mM $CaCl_2$ adjusted to a pH of 7.5, the packing material is ready for equilibrating according to the equilibrating procedures described above.

Finally, regenerating Reactive Red 120-Agarose gel in accordance with the present invention involves first sequentially causing a solution comprising 2 M NaCl and then a solution comprising 5 M urea to flow over spent Reactive Red 120-Agarose gel thereby removing clostripain and pigment impurities from the column. Then by causing a solution comprising 1.5 M NaCl, 5 mM Tricine, and 5 mM $CaCl_2$ adjusted to pH 7.5, the Reactive Red 120-Agarose gel is equilibrated and ready for eluting additional second collected solutions.

Preferred exemplary embodiments of the present invention incorporate additional process steps associated with preparing the crude collagenase solution and the first collected solution for each subsequent eluting step. For example, added process steps can be utilized which are designed to remove any high molecular weight and solid components. Accordingly, as illustrated in the more detailed flow diagram of FIG. 2, prior to eluting the stabilized crude collagenase solution and subsequent to digesting nucleic acids with deoxyribonuclease (DNase), preferably the DNase digested crude collagenase solution is dialyzed utilizing dialysis tubing having a molecular weight cutoff of 50,000. The dialyzing solution is preferably a stabilizing solution comprising 0.15 M potassium phosphate, 5 mM arginine and 1 mM $CaCl_2$, and the dialysis is carried out according to methods known in the art. Then, centrifuging the resulting dialysate provides a supernatant of dialyzed and stabilized crude collagenase solution. In order to prepare this solution for eluting on hydroxylapatite, the supernatant solution of 0.15 M potassium phosphate, 5 mM arginine, and 1 mM $CaCl_2$ is adjusted with a suitable non-ionic surfactant to a surfactant concentration of about 0.01 wt. %.

Preferred processes of the present invention further include similar dialyzing and centrifuging steps in connection with preparing the first collected solution for eluting on Sephacryl s-200 HR packing material. Subsequent to pooling the analyzed enzyme fractions eluted from the hydroxylapatite column, the resulting first collected solution is concentrated utilizing concentration techniques or other similar methods known in the art. The concentrated first collected solution is then dialyzed against a solution comprising about 5 mM arginine and about 1 mM $CaCl_2$ utilizing dialysis tubing preferably having a 50,000 molecular weight cutoff This step is followed by dialyzing the first collected solution again with another solution. Preferred dialyzing solutions are solutions comprising about 1.5 M NaCl, about 5 mM Tricine, about 5 mM $CaCl_2$, and about 5 mM arginine buffered to pH 7.5. The dialysate obtained from the second dialysis step is then centrifuged and filtered through a 0.45 micron filter prior to eluting the resulting dialyzed, centrifuged and filtered first collected solution.

In accordance with the present invention, concentrating, dialyzing, and centrifuging steps similar to those associated with preparing the stabilized crude collagenase solution and the first collected solution can be carried out in connection with providing the purified collagenase solution. Accordingly, subsequent to eluting the second collected solution on Reactive Red 120-Agarose gel and pooling the analyzed enzyme fractions to form purified collagenase, preferred processes further include forming a collagenase concentrate by utilizing known concentration methods and instrumentation such as standard cell concentrators. Then, the collagenase concentrate is dialyzed utilizing dialysis tubing having a 50,000 molecular weight cutoff against Plasmalyte A ®, an electrolyte solution available from Baxter-IV Systems, containing 1 mM CaCl₂, pH 7.4. Finally, filtering the dialyzate through a 0.20 micron filter and centrifuging the filtrate provide a centrifuged supernatant of purified collagenase which is substantially free of pigment and proteolytic enzyme impurities.

Those skilled in the art will appreciate that by performing each of the eluting steps as well as the concentrating, dialyzing, and centrifuging steps, the purity of the collagenase can be increased. Accordingly, after performing the above-described purification procedure of the present invention, the resulting purified collagenase includes only trace amounts of residual trypsin and clostripain activities. In fact these trace amounts constitute less than 1% of the total protein of the purified collagenase. SDS-gel electrophoresis studies demonstrate the high purity of collagenase purified according to the present invention. Furthermore, isoelectric focusing analyses confirm that the isomeric forms of the collagenase found in the crude collagenase solution are maintained in the purified collagenase. This assures that the purified collagenase retains its ability to hydrolyze a full range of collagen proteins.

Those skilled in the art will also appreciate that the two step gradient process associated with eluting the stabilized crude collagenase solution on hydroxylapatite significantly reduces the volume of first and second eluting solutions required to provide the first collected solution. Moreover, the presence of non-ionic surfactant in the first and second solutions assures the wasteless and rapid elution of the stabilized crude collagenase solution without cracking or otherwise rendering the hydroxylapatite column useless. Finally, by incorporating stabilizing CaCl₂ and arginine in the eluting solutions and crude collagenase, autocatalytic loss of collagenase is avoided and high yields of purified collagenase are maintained.

As mentioned above, the purified collagenase of the present invention has a wide range of applications related to hydrolyzing connective tissue. These applications include isolating cells from connective tissue and implanting the isolated cells for in vivo therapeutic treatments. Advantageously, by removing non-collagen specific enzyme activities, such as trypsin and clostripain, the present invention provides collagenase which is substantially free of proteases which may degrade collagenase, thus eliminating the autocatalytic degradation properties which are characteristic of crude collagenase. Furthermore, because the processes of the present invention eliminate sensitizing antigens and other toxins, the purified collagenase of the present invention will not result in anaphylactic shock or related immunological reactions if present in cells or tissues implanted or digested in vivo.

The following nonlimiting example illustrates an exemplary enzyme purification process of the present invention and further presents data demonstrating the retention of isomer forms and the high yield associated with the present invention.

EXAMPLE

Exemplary Collagenase Purification Procedure

A hydroxylapatite chromatography column was prepared and a solution of crude collagenase was stabilized and chromatographed on the column as follows. Three liters of hydroxylapatite Bio-gel HT packing material purchased from Bio Rad as product no. 130-0151 was suspended in a solution containing 1.0 M NaCl and 0.01 wt. % Tween 20 and then allowed to settle for at least one hour. The supernatant was removed and the suspending step was repeated. After removing the second supernatant, the hydroxylapatite was resuspended in a solution containing 0.15 M potassium phosphate and 0.01 wt. % Tween 20 adjusted to pH 6.7.

The suspended hydroxylapatite packing material was packed into a glass chromatography column measuring 10 cm in diameter and 50 cm long. A 20 gram portion of crude collagenase, purchased from Boehringer Mannheim, was dissolved in 400 mL of a solution containing 0.15 M potassium phosphate and 5 mM magnesium chloride adjusted to pH 6.7. A 1 mL portion of this solution was diluted and the solution's optical density was determined at 260 nm, 280 nm, and 410 nm.

Then, 16000 units (40 units/ml) of deoxyribonuclease (DNase) was added to the crude collagenase solution and the resulting solution was gently mixed for 40 minutes to digest the deoxyribose nucleic acid in the solution. Following the digestion a 1 mL portion of the digested solution was diluted and the optical density of the solution was determined at 260 nm, 280 nm, and 410 nm.

Next, the DNase digested solution of crude collagenase was dialyzed overnight against 4000 mL of a solution containing 0.15 M potassium phosphate, 5 mM arginine, and 1 mM CaCl₂ adjusted to pH 6.7. The dialyzed sample was then centrifuged at 20,000 rpm for 20 minutes at 4° C. and the supernatant was collected and adjusted to a Tween 20 concentration of 0.01 wt. %.

The collected sample of stabilized crude collagenase was applied to the top of the hydroxylapatite packed chromatography column using a peristaltic pump at a flow rate of 1.3 cm/hr. The collection end of the hydroxylapatite column was fitted to a fraction collector for collecting fractions of 17 mL and to a UV detector in order to detect material at specific wavelengths eluted from the column. The collected sample was eluted with a solution containing 0.15 M potassium phosphate and 0.01 wt. % Tween 20 at a flow rate of 1.3 cm/hr. The collagenase activity of fractions showing a UV absorbance at 280 nm (first peak) was monitored using a FALGPA (furyl acryloyl Leu-Gly-Pro-Ala) assay. When the column is performing normally, no collagenase activity should be found in the first peak.

Once the UV absorbance at 280 nm dropped to 10% of full scale, the eluting solution was changed to a second solution containing 0.4 M potassium phosphate, 0.01 wt. % Tween 20 and 1 mM CaCl₂ adjusted to pH 6.7. Fractions which were collected using this second eluting solution and showing a UV absorbance at 280 nm (second peak) were adjusted with a solution of 100 mM arginine to provide collected fractions having an arginine concentration of 5 mM. These fractions were assayed for collagenase, trypsin, and clostripain activity until no UV absorbance (the second peak) was detected.

Prior to testing for each of the enzymes the collected fractions were diluted 5-fold for the trypsin and collagenase assays and 32-fold for the clostripain assay. This dilutes the phosphate concentration sufficiently to preclude precipitation with CaCl₂ in the assay buffer to prevent interference with the assay.

The clostripain activity usually appears at the tail end of the peak. As the absorbance decreased and the clostripain activity increased, the ratio of clostripain activity (measured using BAEE, benzoyl L-arginine ethyl ester substrate) to collagenase activity (measured using FALGPA substrate) was determined. All fractions having a ratio of less than or equal to 0.25, and having a collagenase activity greater than 15 μkat/L (micromoles of FALGPA substrate hydrolyzed per second at pH 7.5 at 37 C) were pooled. After all the fractions were pooled to provide a first collected solution, 1 mL of the first collected solution was diluted and the absorbance at 260 nm, 280 nm, and 410 nm was determined. The ratio of the absorbance at 260 nm to 280 nm was less than 0.5 indicating successful removal of nucleic acid materials, and the ratio of the absorbance at 410 nm to 280 nm was less than 0.05 indicating successful removal of pigments.

The first collected sample of pooled fractions was concentrated to 60 mL using an Amicon stir cell concentrator and a PM 10 membrane sterilized with 5.0 wt. % formaldehyde and 25% ethanol. The concentrated 60 mL sample was then dialyzed against 6000 mL of a solution containing 5 mM arginine and 1 mM $CaCl_2$ overnight. The dialysis solution was then changed to a solution containing 1.5 M NaCl, 5 mM Tricine, 5 mM $CaCl_2$, and 5 mM arginine adjusted to pH 7.5, and the dialysis was continued for 2 additional hours. The dialyzed sample was then collected and centrifuged at 20,000 rpm for 20 minutes at 4° C. and the resulting supernatant was collected and filtered through a 0.45 micron filter.

The filtered solution was then chromatographed on a gel filtration column in order to further separate collagenase from other proteolytic enzymes. This gel filtration separation procedure involved first packing two chromatography columns with Sephacryl s-200 HR by suspending 6 liters of Sephacryl s-200 HR in a solution containing 1.5 M NaCl, 5 mM $CaCl_2$, and 5 mM Tricine adjusted to pH 7.5 and then pouring the suspension into two glass columns connected in series at their bases and sized at 5 cm × 100 cm. The outlet of the second column was connected to a fraction collector and a UV detector for detecting the UV absorbance of the solution eluted from the second column. Using a peristaltic pump, the packed columns were equilibrated by passing through the first and second columns about 8 L of a solution containing 1.5 M NaCl, 5 mM Tricine, and 5 mM $CaCl_2$ adjusted to pH 7.5 at a flow rate of about 4 cm/hr.

Then the filtered sample obtained from the hydroxylapatite column was applied to the top of the first column and eluted through both columns with a solution containing 1.5 M NaCl, 5 mM Tricine, and 5 mM $CaCl_2$ adjusted to pH 7.5. Each fraction of the collected material was assayed for collagenase, trypsin, and clostripain activity. Fractions having a collagenase activity of greater than 1.240 μkat/L were pooled. For fractions having a collagenase activity of less than 1.240 μkat/L, the ratio of clostripain activity to collagenase activity was determined and fractions having a ratio of less than 2.0 and a trypsin activity of less than 1.170 μkat/L measured using a BAPNA (benzoyl L-arginine p-nitroanilide) substrate were pooled. The sample obtained from the pooled fractions was then passed through a 0.45 micron filter.

A chromatography column was packed with Reactive Red 120-Agarose gel, type 3000 Cl by suspending 500 ml of the packing material in a solution containing 1.5 M NaCl, 5 mM Tricine, and 5 mM $CaCl_2$ adjusted to pH 7.5 and pouring the suspension into a 5 cm × 25 cm glass column. The outlet of the glass column was fitted to a fraction collector and a UV detector for detecting the UV absorbance of material eluted from the column.

The column was equilibrated by passing about 2 L of the equilibrating solution over the packing using a peristaltic pump at 2.1 cm/hr. Then the filtered sample obtained from the pooled fractions off the gel filtration columns was applied to the top of the Reactive Red 120-Agarose packed column and eluted with a solution containing 1.5 M NaCl, 5 mM Tricine, and 5 mM $CaCl_2$, adjusted to pH 7.5. Collected fractions having a UV absorbance at 280 nm were assayed for collagenase and clostripain activity. All fractions having a collagenase activity of greater than 1.240 μkat/L were pooled. The pooled fractions were then concentrated to a collagenase activity of 900 μkat/L using an Amicon stir cell concentrator and a PM 10 membrane.

The concentrated solution was then dialyzed overnight against Plasmalyte A ® electrolyte solution containing 1 mM $CaCl_2$, and centrifuged at 20,000 rpm for 20 minutes. The supernatant was collected, analyzed for collagenase and clostripain activity, and finally lyophilized for long term storage.

Table I provides the associated data relating to collagenase, trypsin, and clostripain activity as well as DNA impurity content as indicated by the change in UV absorbance of the collagenase solution prior to each step of the above described purification process.

TABLE I

| | COLLAGENASE PURIFICATION RECOVERY | | | | | | |
|---|---|---|---|---|---|---|---|
| | COLLAGENASE nkat/mg* | TRYPSIN nkat/mg* | CLOSTRIPAIN nkat/mg* | DNA ug/mg* | 260** | 280** | 410** |
| CRUDE COLLAGENASE | 33.0 | 7.7 | 85.5 | 11.4 | 0.89 | 1.29 | 0.177 |
| AFTER HYDROXY- APATITE | 37.9 | 4.5 | 61.3 | 1.5 | 0.41 | 1.48 | 0.013 |
| AFTER GEL FILTRATION | 38.9 | 0.2 | 4.1 | — | 0.31 | 0.99 | 0.009 |
| FINAL PRODUCT | 42.7 | 0.2 | 3.8 | 0.8 | 0.29 | 0.95 | 0.008 |

NOTE: *All activities are expressed per mg of protein.
**Optical density of protein solution at 1 mg/ml.

As shown by Table I, the collagenase activity of each solution rose dramatically from 33 nkat/mg of protein in the crude collagenase to a final activity of 42.7 nkat/mg of protein. In contrast, the trypsin and clostripain activities were dramatically lowered from 7.7 and 85.5 nkat/mg protein, respectively, to a final concentration of 0.2 and 3.8 nkat/mg protein. Furthermore, the DNA content dropped from 11.4 μg/mg protein to a final 0.8 μg/mg protein. The pigment content also dropped dramatically as demonstrated by the solution absorbance at 410 nm.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is limited only by the following claims.

We claim:

1. A process for purifying crude collagenase compositions containing collagenase, pigment, toxins, bacterial material, and proteolytic enzyme impurities including clostripain, trypsin, and caseinase, said process comprising the steps of:

applying a stabilized crude collagenase solution to a column containing hydroxylapatite packing;

eluting pigment and caseinase from the hydroxylapatite packing with a first solution comprising about 0.05 M to about 0.3 M phosphate, buffered to about pH 6 to about pH 8, and a nonionic surfactant;

eluting collagenase, clostripain, and trypsin with a second solution comprising about 0.35 M to about 0.5 M phosphate, buffered to about pH 6 to about pH 8, and a nonionic surfactant, to provide a first collected solution;

applying said first collected solution to a column containing gel filtration packing;

eluting collagenase and clostripain with a third solution comprising a neutral pH buffer, to provide a second collected solution;

applying said second collected solution to a column containing Reactive Red 120-Agarose packing; and eluting collagenase with a fourth solution comprising a neutral pH buffer, to provide a solution comprising purified collagenase.

2. The process of claim 1 wherein said stabilized crude collagenase solution comprises collagenase, $CaCl_2$, and arginine.

3. The process of claim 1 further comprising the step of adding deoxyribonuclease to said stabilized crude collagenase solution in an amount sufficient to provide a deoxyribonuclease activity of about 40 u/mL.

4. The process of claim 1 further comprising the steps of:

dialyzing said stabilized crude collagenase solution against a solution comprising about 0.15 M potassium phosphate, about 5 mM arginine, and about 1 mM $CaCl_2$, buffered to about pH 6.7, to provide a first dialysate; and centrifuging said first dialysate to provide a supernatant comprising dialyzed and stabilized crude collagenase solution.

5. The process of claim 4 further comprising the steps of:

concentrating said first collected solution;

dialyzing the concentrated first collected solution with a solution comprising NaCl, Tricine, $CaCl_2$, and arginine, buffered to about pH 7.5, to provide a second dialysate; and centrifuging said second dialysate to provide a supernatant comprising dialyzed first collected solution.

6. The process of claim 1 wherein said first solution comprises about 0.15 M potassium phosphate, about 0.01 wt. % nonionic surfactant, and about 1 mM $CaCl_2$, buffered to about pH 6.7.

7. The process of claim 1 wherein said second solution comprises about 0.4 M potassium phosphate, about 0.01 wt. % nonionic surfactant, and about 1 mM $CaCl_2$, buffered to about pH 6.7.

8. The process of claim 1 wherein said third solution comprises about 1.5 M NaCl, about 5mM $CaCl_2$, and about 5 mM Tricine, buffered to about pH 7.5.

9. The process of claim 1 wherein said fourth solution comprises about 1.5 M NaCl, about 5mM $CaCl_2$, and about 5 mM Tricine, buffered to about pH 7.5.

10. An process for purifying collagenase compositions comprising the steps of:

digesting a crude collagenase solution containing collagenase, pigment, toxins, bacterial materials, and proteolytic enzyme impurities, including clostripain, trypsin, and caseinase, in a solution comprising magnesium chloride, potassium phosphate, and deoxyribonuclease;

dialyzing the digested crude collagenase solution against a solution comprising about 0.15 M potassium phosphate, about 5 mM arginine, and about 1 mM $CaCl_2$, buffered to about pH 6.7, to provide a dialysate;

centrifuging said dialysate to provide a supernatant;

applying said supernatant to a hydroxylapatite packed chromatography column;

eluting pigment with a first solution comprising about 0.15 M potassium phosphate, about 0.01 wt. % nonionic surfactant, and about 1 mM $CaCl_2$, buffered to about pH 6.7;

eluting proteolytic enzyme impurities and collagenase with a second solution comprising about 0.4 M potassium phosphate, about 0.01 wt. % nonionic surfactant, and about 1 mM $CaCl_2$, buffered to about pH 6.7, to provide a first collected solution;

applying said first collected solution to a gel filtration packed chromatography column;

eluting collagenase and clostripain with a third solution comprising about 1.5 M NaCl, about 5 mM $CaCl_2$, and about 5mM Tricine, buffered to about pH 7.5, to provide a second collected solution;

applying said second collected solution to a Reactive Red 120-Agarose packed chromatography column; and eluting purified collagenase with a fourth solution comprising about 1.5 M NaCl, about 5mM $CaCl_2$, and about 5 mM Tricine, buffered to about pH 7.5.

11. The process of claim 10 further comprising the step of regenerating said hydroxylapatite packing with sodium hydroxide.

12. The process of claim 10 further comprising the step of regenerating said gel filtration packing with sodium hydroxide.

13. The process of claim 10 further comprising the steps of:

regenerating said Reactive Red 120-Agarose packing first with sodium chloride and then with urea.

14. The process of claim 10 further comprising the steps of:

collecting fractions eluted from hydroxylapatite;

assaying said fractions for collagenase, trypsin, and clostripain activity; and pooling collected fractions having a collagenase activity greater than 15 μkat/L and a ratio of clostripain activity to collagenase activity less than or equal to 0.25, to provide said first collected solution.

15. The process of claim 10 further comprising the steps of:

collecting fractions eluted from gel filtration packing;

assaying said fractions for collagenase, trypsin, and clostripain activity; and pooling collected fractions having a collagenase activity greater than 1.240 μkat/L or a ratio of clostripain activity to collagenase activity less than or equal to 2.0 and trypsin activity less than 1.170 μkat/L, to provide said second collected solution.

16. The process of claim 10 further comprising the steps of:

collecting fractions eluted from Reactive Red 120-Agarose packing;

assaying said fractions for collagenase, trypsin, and clostripain activity; and pooling collected fractions having a collagenase activity greater than 1.24 μkat/L.

* * * * *